(12) United States Patent
Wang

(10) Patent No.: US 11,254,687 B2
(45) Date of Patent: Feb. 22, 2022

(54) ORGANIC LIGHT-EMITTING MATERIAL AND MANUFACTURING METHOD THEREOF, AND ORGANIC LIGHT-EMITTING DEVICE

(71) Applicant: WUHAN CHINA STAR OPTOELECTRONICS SEMICONDUCTOR DISPLAY TECHNOLOGY CO., LTD., Hubei (CN)

(72) Inventor: Yamin Wang, Hubei (CN)

(73) Assignee: WUHAN CHINA STAR OPTOELECTRONICS SEMICONDUCTOR DISPLAY TECHNOLOGY CO., LTD., Hubei (CN)

(*) Notice: Subject to any disclaimer, the term of this patent is extended or adjusted under 35 U.S.C. 154(b) by 355 days.

(21) Appl. No.: 16/607,647

(22) PCT Filed: Aug. 20, 2019

(86) PCT No.: PCT/CN2019/101491
§ 371 (c)(1),
(2) Date: Oct. 23, 2019

(87) PCT Pub. No.: WO2020/232852
PCT Pub. Date: Nov. 26, 2020

(65) Prior Publication Data
US 2021/0403481 A1    Dec. 30, 2021

(30) Foreign Application Priority Data
May 20, 2019    (CN) .......................... 201910416911.5

(51) Int. Cl.
 *H01L 51/50* (2006.01)
 *C07D 498/00* (2006.01)
 *H01L 51/00* (2006.01)

(52) U.S. Cl.
 CPC ........ *C07D 498/00* (2013.01); *H01L 51/0054* (2013.01); *H01L 51/0069* (2013.01); *H01L 51/5012* (2013.01); *H01L 2251/552* (2013.01)

(58) Field of Classification Search
 None
 See application file for complete search history.

(56) References Cited

U.S. PATENT DOCUMENTS

| 8,119,814 B2 | 2/2012 | Shin |
| 2010/0308315 A1 | 12/2010 | Arakane et al. |
| 2012/0013700 A1 | 1/2012 | Horiuchi |
| 2016/0276602 A1* | 9/2016 | Yoshinaga .......... H01L 51/0059 |
| 2016/0322606 A1* | 11/2016 | Jin ...................... H01L 51/0061 |

FOREIGN PATENT DOCUMENTS

| CN | 101026226 A | 8/2007 |
| CN | 102365253 A | 2/2012 |

OTHER PUBLICATIONS

Wendu Ding, et al; "Computational Design of Intrinsic Molecular Rectifiers Based on Asymmetric Functionalization of N-Phenylbenzamide", Journal of Chemical Theory and Computation; Published Nov. 3, 2015; pp. 588-5896.

Yoshihito Kunugi, et al; "Characteristics of Thin-Film Transistors Based on 2,8-Disubstituted Chrysene Derivatives with Polymer-Treated $SIO_2$ Dielectric Layers", Electrochemistry, 81(5), pp. 402-404, May 2013.

* cited by examiner

*Primary Examiner* — Dung A. Le

(57) ABSTRACT

An organic light-emitting material and the manufacturing method thereof, and an organic light-emitting device are disclosed. The organic light-emitting material includes a benzophenanthrene derivative, which has good planarity and strong visible $\pi$-$\pi$* absorption ability and has a high quantum yield of blue light-emitting capability as well. Therefore, a benzophenanthrene derivative having a large $\pi$-conjugated system has high-efficiency electron transporting properties, and its high electron-withdrawing group increases electron mobility rate and effectively improve the light-emitting efficiency of the organic light emitting device.

8 Claims, 2 Drawing Sheets

ORGANIC LIGHT-EMITTING MATERIAL AND MANUFACTURING METHOD THEREOF, AND ORGANIC LIGHT-EMITTING DEVICE

FIELD OF INVENTION

The present application relates to the field of display technologies, and more particularly to an organic light-emitting material and a manufacturing method thereof, and an organic light-emitting device.

BACKGROUND

At present, organic light-emitting materials have achieved world-renowned achievements, and many domestic companies have realized the successful lighting of flexible OLED display panels, and various flexible panels have been fabricated. However, at present, the light-emitting material of the flexible OLED display panel has some problems regardless of cost, stability of the organic light-emitting device, or durability of the light-emitting material. Therefore, it is very important to enrich and develop main materials of the light-emitting layer in the organic light-emitting device, and further developments of main materials of the light-emitting layer with long life and high stability of efficiency and performance are still an important goal of researchers.

SUMMARY

In order to solve the above technical problems, the present application provides an organic light-emitting material and a manufacturing method for the same, and an organic light-emitting device. The organic light-emitting material comprises a benzophenanthridine derivative having a large π-conjugated system to improve light-emitting efficiency.

The present application provides an organic light-emitting material comprising a benzophenanthrene derivative having a large π-conjugated system.

In one embodiment, the benzophenanthrene derivative is represented by the following molecular structure formula:

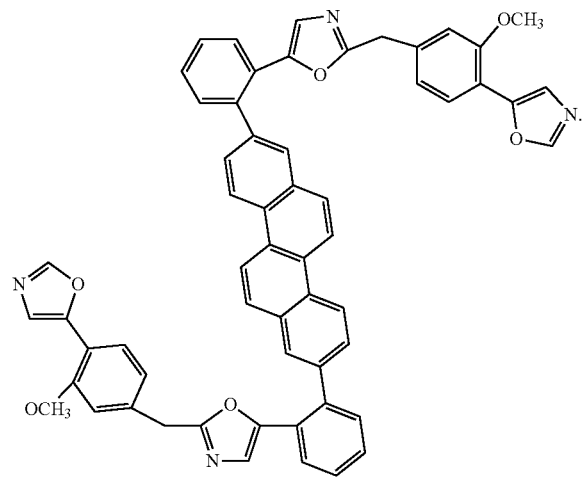

The present application further provides a manufacturing method for manufacturing the organic light-emitting material, comprising the following steps: providing a boronic acid derivative of benzophenanthrene and a bromide of dioxazole; adding boric acid, the boronic acid derivative of benzophenanthrene, the bromide of dioxazole, potassium carbonate, and N,N-dimethylformamide solvent to a round-bottom flask under protection of nitrogen, and continuously stirring for 1-3 hours to obtain a first mixture solution; rising a temperature of the first mixture solution to 40-70° C., and adding tetrakis(triphenylphosphine)palladium to the first mixture solution and then continuously raising the temperature thereof to 80-100° C. to react for 24-96 hours and obtain a first reaction solution; and cooling the first reaction solution to room temperature, and then performing suction filtration and drying to obtain the organic light-emitting material.

In one embodiment of the present application, the step of providing the boronic acid derivative of benzophenanthrene comprises dissolving a benzophenanthrene compound in dichloromethane and continuously stirring thereof, and then adding dichloromethane solution of anhydrous hydrogen bromide to react for 3-12 hours and obtain a second reaction solution; adding sodium fulfate to the second reaction solution and sufficiently stirring thereof, and obtaining a third reaction solution after standing; extracting the third reaction solution with dichloromethane, and then precipitating white solids with ethanol and drying thereof, thereby obtaining an intermediate of a benzophenanthrene derivative; completely dissolving the intermediate of the benzophenanthrene derivative in a tetrahydrofuran solution to obtain a fourth reaction solution, and then lowering a temperature of the fourth reaction solution to maintain thereof at −70° C. to −90° C., then dropping a catalyst of butyllithium therein until the fourth reaction solution becomes yellow, and then reacting for 2-3 hours; dropping trimethylborate in the fourth reaction solution until the fourth reaction solution becomes transparent, and then reacting for 1-3 hours to obtain a fifth reaction solution; and adding dilute hydrochloric acid to the fifth reaction solution and stirring thereof, then precipitating white solids through suction filtering and drying thereof, thereby obtaining the boronic acid derivative of benzophenanthrene.

In one embodiment of the present application, the benzophenanthrene compound comprises at least one of 1,2-benzphenanthrene, 2,3,6,7-benzphenanthrene, 9,10-benzphenanthrene, and dodecahydrotriphenylene.

In one embodiment of the present application, the benzophenanthrene compound comprises 1,2-benzphenanthrene, and the intermediate of the boronic acid derivative of benzophenanthrene is represented by the following molecular structure formula:

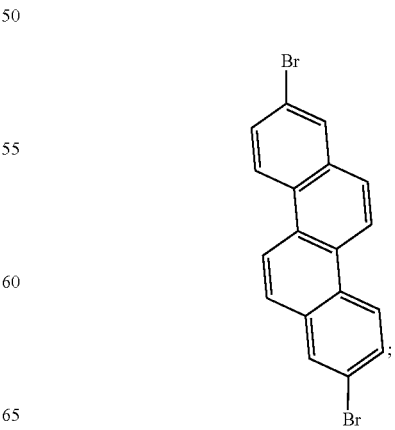

and the boronic acid derivative is represented by the following molecular structure formula:

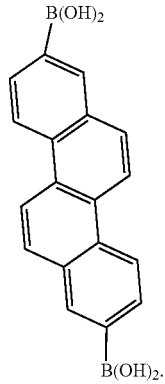

In one embodiment of the present application, the step of providing the bromide of dioxazole comprises providing an aryl-isothiocyanate compound and a keto-azide compound; sequentially adding the aryl-isothiocyanate compound and a tetrahydrofuran solution to a flask under protection of argon, and then adding copper powders therein to obtain a second mixture solution; heating up the second mixture solution to 40° C., until the second mixture solution becomes blue; forming a keto-azide compound solution by dissolving the keto-azide compound in a tetrahydrofuran solution, and dropping the keto-azide compound solution in the second mixture solution to react for 6-10 hours at a fixed temperature until thereof becomes dark brown; and obtaining the bromide of dioxazole by suction filtering and drying.

In one embodiment of the present application, the aryl-isothiocyanate is represented by the following molecular structure formula:

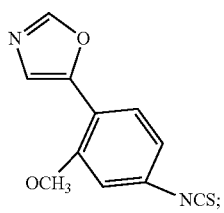

the keto-azide compound is represented by the following molecular structure formula:

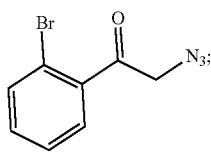 [SMILES: [N-]=[N+]=NCC(=O)c1ccccc1Br]

and the bromide of dioxazole is represented by the following molecular structure formula:

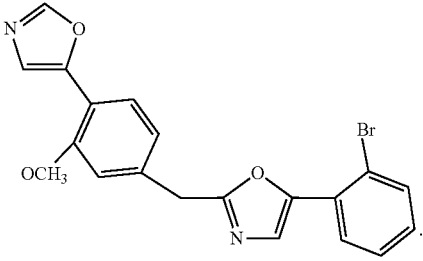 [SMILES: COc1cc(Cc2ncc(-c3ccccc3Br)o2)ccc1-c1cnco1]

The present application further provides an organic light-emitting device comprising the above organic light-emitting material.

In one embodiment, the organic light-emitting device comprises a first electrode; a hole injecting layer disposed over the first electrode; a hole transporting layer disposed over the hole injecting layer; a light-emitting layer disposed over the hole transporting layer, wherein the light-emitting layer comprises the organic light-emitting material; an electron transporting layer disposed over the light-emitting layer; an electron injecting layer disposed over the electron transporting layer; and a second electrode disposed over the electron injecting layer.

In the organic light-emitting material and the manufacturing method thereof, and the organic light-emitting device of the present application, the organic light-emitting material with the benzophenanthrene derivative is obtained by the manufacturing method through the Suzuki reaction, which has good planarity and strong visible π-π* absorption ability. At the same time, it has a high quantum yield of blue light-emitting capability. Therefore, a benzophenanthrene derivative having a large π-conjugated system has high-efficiency electron transporting properties, and its high electron-withdrawing group increases electron mobility rate and effectively improve the light-emitting efficiency of the organic light emitting device.

BRIEF DESCRIPTION OF DRAWINGS

To detailly explain the technical schemes of the embodiments or existing techniques, drawings that are used to illustrate the embodiments or existing techniques are provided. Apparently, the illustrated embodiments are just a part of those of the present disclosure. It is easy for any person having ordinary skill in the art to obtain other drawings without labor for inventiveness.

Figure 1:
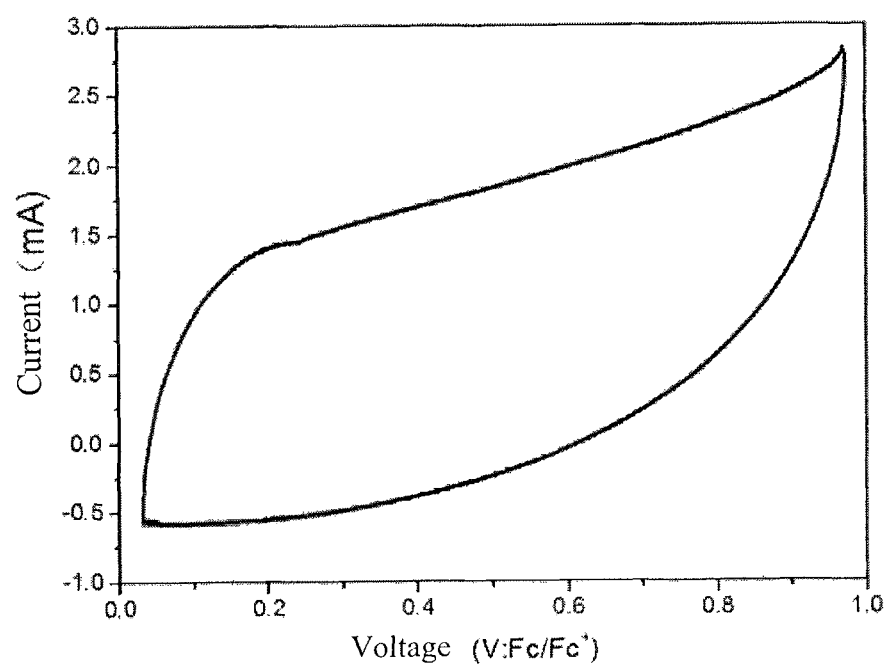
FIG. 1 is a waveform diagram of an organic light-emitting material of the present application obtained by cyclic voltammetry.

1: organic light-emitting device; 11: first electrode; 12: hole injecting layer; 13: hole transporting layer; 14: light-emitting layer; 15: electron transporting layer; 16: electron injecting layer; and 17: second electrode.

DETAILED DESCRIPTION

To detailly explain the technical schemes of the embodiments or existing techniques, drawings that are used to illustrate the embodiments or existing techniques are provided. Apparently, the illustrated embodiments are just a part of those of the present disclosure. It is easy for any person having ordinary skill in the art to obtain other drawings without labor for inventiveness.

In one embodiment, an organic light-emitting material of the present application comprises a benzophenanthrene derivative having a large π-conjugated system, wherein an example of the benzophenanthrene derivative is represented by the following molecular structure formula:

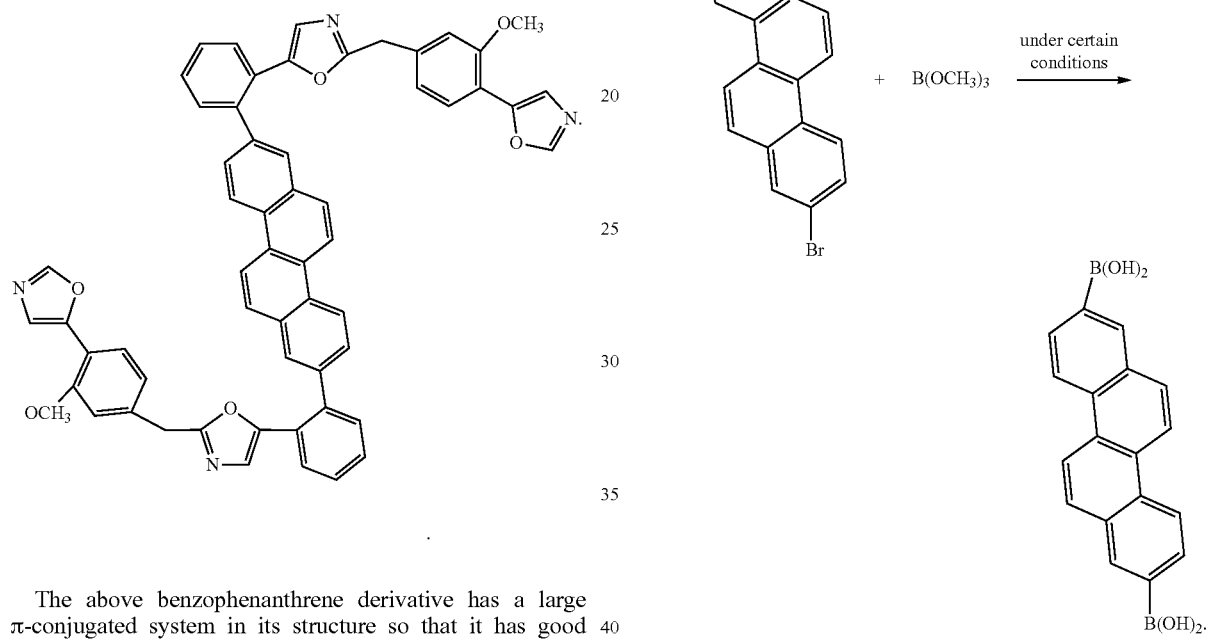

The above benzophenanthrene derivative has a large π-conjugated system in its structure so that it has good planarity and strong visible π-π* absorption ability. At the same time, it has a high quantum yield of blue light-emitting capability. Therefore, a benzophenanthrene derivative having a large π-conjugated system has high-efficiency electron transporting properties, and its high electron-withdrawing group increases electron mobility rate and effectively improve the light-emitting efficiency.

The present application also provides a manufacturing method for manufacturing the organic light-emitting method comprising the benzophenanthrene derivative, comprising the following steps:

providing a boronic acid derivative of benzophenanthrene and a bromide of dioxazole;

The step of providing the boronic acid derivative of benzophenanthrene comprises dissolving a benzophenanthrene compound in dichloromethane, and the benzophenanthrene derivative comprises at least one of 1,2-benzphenanthrene, 2,3,6,7-benzphenanthrene, 9,10-benzphenanthrene, and dodecahydrotriphenylene. In this embodiment, 1,2-benzophenanthrene is taken as an example to describe the manufacturing method of the present application. First, an intermediate of 1,2-benzophenanthrene is chosen, and a boronic acid derivative of the 1,2-benzophenanthrene is formed by the intermediate of 1,2-benzophenanthrene, and synthesis of the boronic acid derivative of the 1,2-benzophenanthrene is represented by the following chemical formula:

Referring to the chemical formula for synthesizing the boronic acid derivative of the 1,2-benzophenanthrene, a benzophenanthrene compound is dissolved in dichloromethane and continuously stirred, and then dichloromethane solution of anhydrous hydrogen bromide is added to react for 3-12 hours and obtain a second reaction solution. Sodium sulfate is added to the second reaction solution and being sufficiently stirred, and a third reaction solution is obtained after standing. The third reaction solution is extracted with dichloromethane, and white solids are then precipitated with ethanol and being dried, thereby obtaining an intermediate of 1,2-benzophenanthrene.

Referring to the chemical formula for synthesizing the boronic acid derivative of the 1,2-benzophenanthrene, the intermediate of 1,2-benzophenanthrene is completely dissolved in a tetrahydrofuran solution to obtain a fourth reaction solution, and then a temperature of the fourth reaction solution is lowered to maintain thereof at −70° C. to −90° C. A catalyst of butyllithium is then dropped therein until the fourth reaction solution becomes yellow and then reacts for 2-3 hours. Trimethyl borate is dropped in the fourth reaction solution until the fourth reaction solution becomes transparent, and then reacts for 1-3 hours to obtain a fifth reaction solution. Dilute hydrochloric acid is added to the fifth reaction solution and the fifth reaction solution is stirred and then white solids are precipitated through suction filtering and drying, thereby obtaining the boronic acid derivative of benzophenanthrene, which is specifically the boronic acid derivative of 1,2-benzophenanthrene.

In the step of providing the bromide of dioxazole comprises providing an aryl-isothiocyanate compound and a keto-azide compound. In the present embodiment, the aryl-isothiocyanate is represented by the following molecular structure formula:

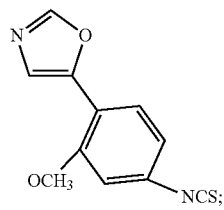

the keto-azide compound is represented by the following molecular structure formula:

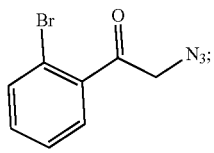 [SMILES: [N-]=[N+]=NCC(=O)c1ccccc1Br]

and the bromide of dioxazole is represented by the following molecular structure formula:

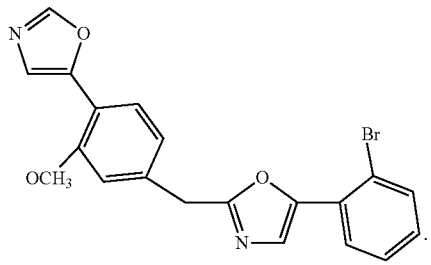 [SMILES: COc1cc(Cc2ncc(-c3ccccc3Br)o2)ccc1-c1cnco1]

Synthesis of the bromide of dioxazole is represented by the following chemical formula:

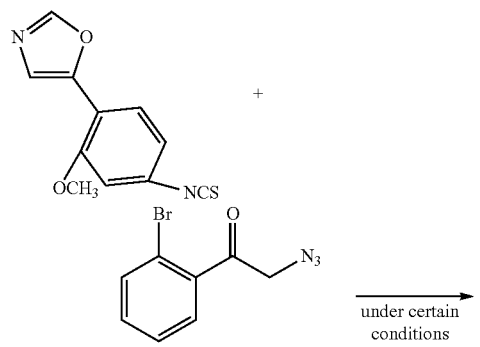

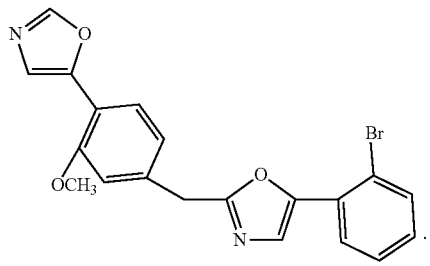

The aryl-isothiocyanate compound and a tetrahydrofuran solution are sequentially added to a flask under the protection of argon, and then copper powders are added therein to obtain a second mixture solution. The second mixture solution is then heated up to 40° C. until the second mixture solution becomes blue. A keto-azide compound solution is formed by dissolving the keto-azide compound in a tetrahydrofuran solution, and the keto-azide compound solution is dropped in the second mixture solution to react for 6-10 hours at a fixed temperature until thereof becomes dark brown. The bromide of dioxazole is then obtained by suction filtering and drying. In the present embodiment, a mole ratio between the aryl-isothiocyanate compound and a keto-azide compound is 1:1.

The organic light-emitting material having a benzophenanthrene derivative is then manufactured by the Suzuki reaction. Formation of the organic light-emitting material having a benzophenanthrene derivative is represented by the following chemical formula:

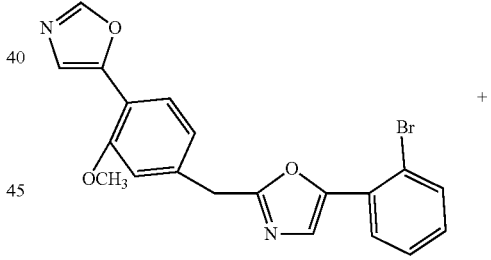

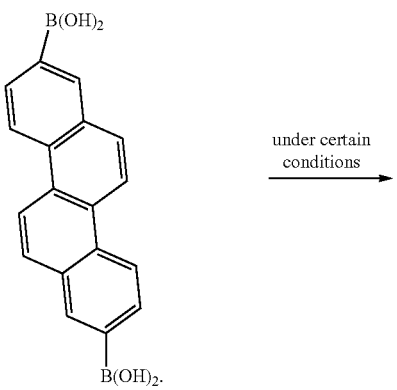

-continued

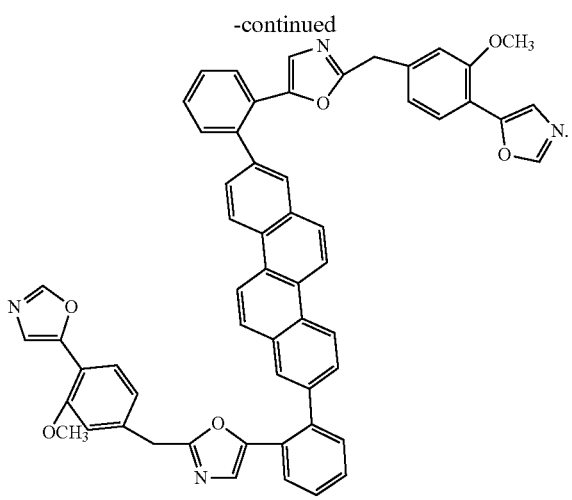

Referring to the chemical formula for forming the organic light-emitting material having a benzophenanthrene derivative, boric acid, the boronic acid derivative of benzophenanthrene, the bromide of dioxazole, potassium carbonate, and N,N-dimethylformamide solvent are added to a round-bottom flask under protection of nitrogen, and is continuously stirred for 1-3 hours to obtain a first mixture solution. A temperature of the first mixture solution is raised to 40-70° C., and tetrakis(triphenylphosphine)palladium is added to the first mixture solution and then the temperature thereof is continuously raised to 80-100° C. to react for 24-96 hours and obtain a first reaction solution. The first reaction solution is cooled to room temperature, and then suction filtration and drying are performed to obtain the organic light-emitting material.

After the organic light-emitting material having a benzophenanthrene derivative is manufactured, properties of the organic light-emitting material having the benzophenanthrene derivative are analyzed. First, functional analysis and energy level calculation of the molecular formula of the organic light-emitting material having the benzophenanthrene derivative are performed. The highest occupied molecular orbital (HOMO) energy level is 4.76 eV and the lowest unoccupied molecular orbital (LUMO) energy level is 1.87 eV, and the energy level difference is 2.89 e V. The HOMO level of 4.76 is lower than that of indium tin oxide (the work function of the indium tin oxide conductive substrate is 5.3). Therefore, the organic light-emitting material having the benzophenanthrene derivative is theoretically compatible with the demands of the work function of the main material of the light-emitting layer the organic light-emitting device. The energy level difference of the oxadiazole to benzoxazole can effectively increase the light-emitting efficiency and light-emitting ability of the device.

Figure 2:
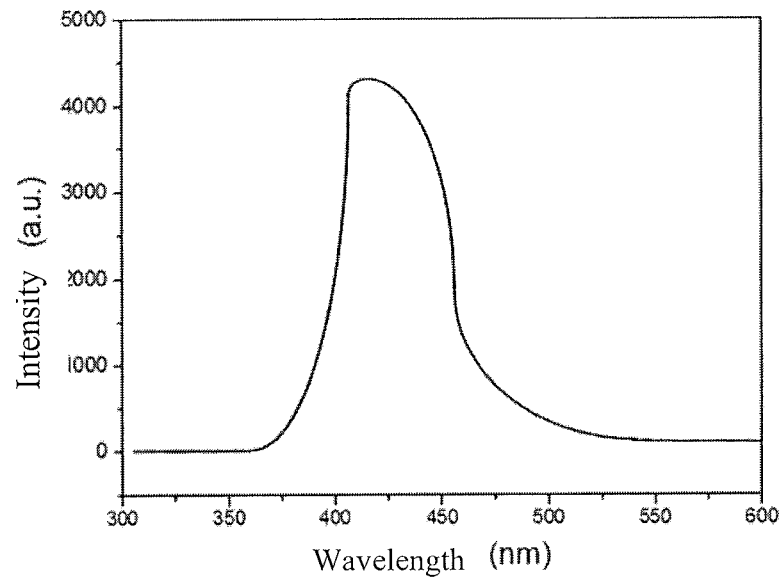
FIG. 2 is a fluorescence spectrum of an organic light-emitting material of the present application.

Next, the organic light-emitting material having the benzophenanthrene derivative is manufactured as an electrolyte solution of 0.1 mol/L and then manufactured as a solution of the organic light-emitting material having tetrahydrofuran of 1×10-6 mol/L and the benzophenanthrene derivative. The solution is subjected to an electrode scanning cycle of 100 m V/s under an argon atmosphere for 10 times to obtain a waveform diagram of cyclic voltammetry, as shown in FIG. 1, which can be seen according to $E_{HOMO}=e(|E\frac{1}{2}|+4.4)$, $E_{LUMO}=E_{HOMO}-|Eg|$; where $Eg=1240/\lambda$, which can be derived from FIG. 2, wavelength $\lambda=429$ nm. The HOMO and LUMO values of 4.76 e V and 1.87 e V respectively of the organic light-emitting material having the benzophenanthrene derivative are calculated, and the energy level difference can effectively balance the charge transport, thereby reconfirming the organic light-emitting material comprising the benzophenanthrene derivative can be used as a material of the light-emitting layer for an organic light-emitting device.

Figure 3:
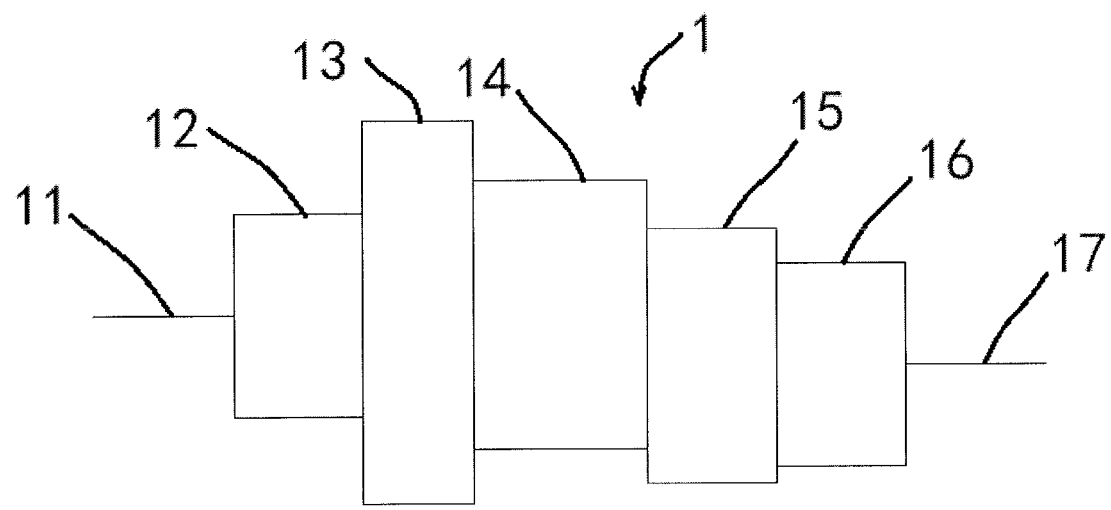
FIG. 3 is a structure diagram of an organic light-emitting device according to an embodiment of the present application.

As shown in FIG. 3, the present application also provides an organic light-emitting device 1 comprising the organic light-emitting material having a benzophenanthrene derivative. In this embodiment, the light-emitting device comprises a first electrode 11, a hole injecting layer 12, a hole transporting layer 13, a light-emitting layer 14, an electron transporting layer 15, an electron injecting layer 16, and a second electrode 17. The hole injecting layer 12 is disposed over the first electrode 11. The hole transporting layer 13 is disposed over the hole injecting layer 12. The light-emitting layer 14 is disposed over the hole transporting layer 13. The light-emitting layer 14 comprises the organic light-emitting material having a benzophenanthrene derivative. The electron transporting layer 15 is disposed over the light-emitting layer 14. The electron injecting layer 16 is disposed over the electron transporting layer 15. The second electrode 17 disposed over the electron injecting layer 16. The first electrode 11 is the anode and the second electrode 17 is the cathode.

While the present disclosure has been described with the aforementioned preferred embodiments, it is preferable that the above embodiments should not be construed as limiting of the present disclosure. Anyone having ordinary skill in the art can make a variety of modifications and variations without departing from the spirit and scope of the present disclosure as defined by the following claims.

What is claimed is:

1. An organic light-emitting device comprises an organic light-emitting material comprising, a benzophenanthrene derivative, wherein the benzophenanthrene derivative is represented by the following molecular structure formula:

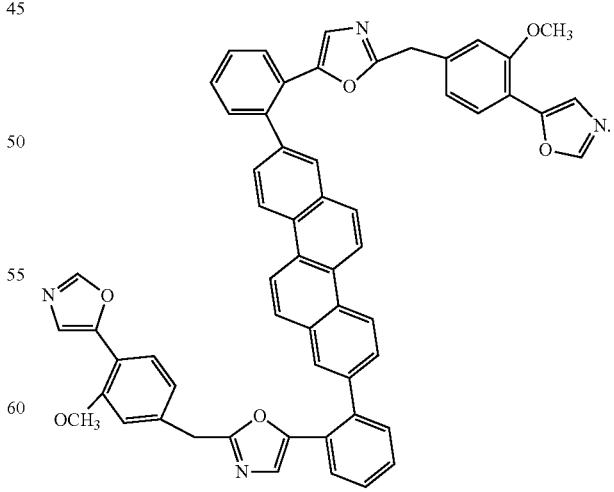

2. A manufacturing method for manufacturing the organic light-emitting material as claimed in claim 1, comprising the following steps:

providing a boronic acid derivative of benzophenanthrene and a bromide of dioxazole;

adding boric acid, the boronic acid derivative of benzophenanthrene, the bromide of dioxazole, potassium carbonate, and N,N-dimethylformamide solvent to a round-bottom flask under the protection of nitrogen, and continuously stirring for 1-3 hours to obtain a first mixture solution;

rising a temperature of the first mixture solution to 40-70° C., and adding tetrakis(triphenylphosphine)palladium to the first mixture solution and then continuously rising the temperature thereof to 80-100° C. to react for 24-96 hours and obtain a first reaction solution; and cooling the first reaction solution to room temperature, and then performing suction filtration and drying to obtain the organic light-emitting material.

3. The manufacturing method as claimed in claim 2, wherein the step of providing the boronic acid derivative of benzophenanthrene comprises:

dissolving a benzophenanthrene compound in dichloromethane and continuously stirring thereof, and then adding dichloromethane solution of anhydrous hydrogen bromide to react for 3-12 hours and obtain a second reaction solution;

adding sodium sulfate to the second reaction solution and sufficiently stirring thereof, and obtaining a third reaction solution after standing;

extracting the third reaction solution with dichloromethane, and then precipitating white solids with ethanol and drying thereof, thereby obtaining an intermediate of a benzophenanthrene derivative;

completely dissolving the intermediate of the benzophenanthrene derivative in a tetrahydrofuran solution to obtain a fourth reaction solution, and then lowering a temperature of the fourth reaction solution to maintain thereof at −70° C. to −90° C., then dropping a catalyst of butyllithium therein until the fourth reaction solution becomes yellow, and then reacting for 2-3 hours;

dropping trimethyl borate in the fourth reaction solution until the fourth reaction solution becomes transparent, and then reacting for 1-3 hours to obtain a fifth reaction solution; and adding dilute hydrochloric acid to the fifth reaction solution and stirring thereof, then precipitating white solids through suction filtering and drying thereof, thereby obtaining the boronic acid derivative of benzophenanthrene.

4. The manufacturing method as claimed in claim 3, wherein the benzophenanthrene compound comprises at least one of 1,2-benzphenanthrene, 2,3,6,7-benzphenanthrene, 9,10-benzphenanthrene, and dodecahydrotriphenylene.

5. The manufacturing method as claimed in claim 4, wherein the benzophenanthrene compound comprises 1,2-benzphenanthrene, and the intermediate of the boronic acid derivative of benzophenanthrene is represented by the following molecular structure formula:

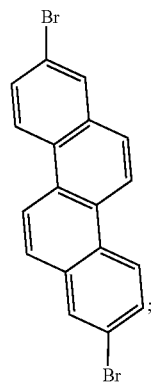 [SMILES: Brc1ccc2c(ccc3c4ccc(Br)cc4ccc23)c1]

and the boronic acid derivative is represented by the following molecular structure formula:

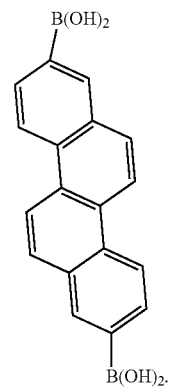 [SMILES: OB(O)c1ccc2c(ccc3c4ccc(B(O)O)cc4ccc23)c1]

6. The manufacturing method as claimed in claim 4, wherein the step of providing the bromide of dioxazole comprises:

providing an aryl-isothiocyanate compound and a keto-azide compound;

sequentially adding the aryl-isothiocyanate compound and a tetrahydrofuran solution to a flask under the protection of argon, and then adding copper powders therein to obtain a second mixture solution;

heating up the second mixture solution to 40° C., until the second mixture solution becomes blue;

forming a keto-azide compound solution by dissolving the keto-azide compound in a tetrahydrofuran solution;

dropping the keto-azide compound solution in the second mixture solution to react for 6-10 hours at a fixed temperature until thereof becomes dark brown; and obtaining the bromide of dioxazole by suction filtering and drying.

7. The manufacturing method as claimed in claim 5, wherein:

the aryl-isothiocyanate is represented by the following molecular structure formula:

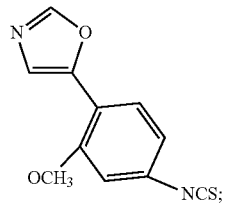

the keto-azide compound is represented by the following molecular structure formula:

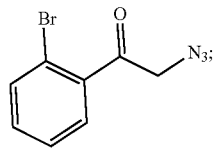 [SMILES: [N-]=[N+]=NCC(=O)c1ccccc1Br]

and the bromide of dioxazole is represented by the following molecular structure formula:

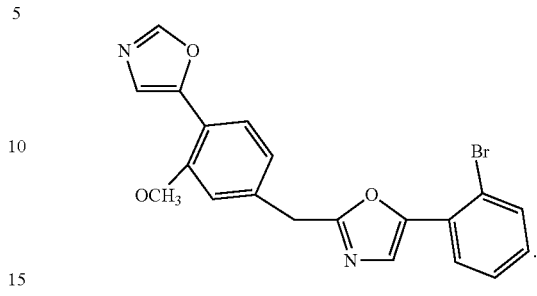

8. The organic light-emitting device as claimed in claim 1, comprising:
   a first electrode;
   a hole injecting layer disposed over the first electrode;
   a hole transporting layer disposed over the hole injecting layer;
   a light-emitting layer disposed over the hole transporting layer, wherein the light-emitting layer comprises the organic light-emitting material;
   an electron transporting layer disposed over the light-emitting layer;
   an electron injecting layer disposed over the electron transporting layer; and
   a second electrode disposed over the electron injecting layer.

* * * * *